(12) United States Patent
Tanaka et al.

(10) Patent No.: US 7,470,824 B2
(45) Date of Patent: Dec. 30, 2008

(54) ADAMANTANE DERIVATIVE AND PROCESS FOR PRODUCING THE SAME

(75) Inventors: Shinji Tanaka, Chiba (JP); Hidetoshi Ono, Chiba (JP); Kouichi Kodoi, Chiba (JP); Naoyoshi Hatakeyama, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 400 days.

(21) Appl. No.: 10/540,547

(22) PCT Filed: Dec. 18, 2003

(86) PCT No.: PCT/JP03/16258

§ 371 (c)(1),
(2), (4) Date: Dec. 13, 2005

(87) PCT Pub. No.: WO2005/058675

PCT Pub. Date: Jul. 15, 2004

(65) Prior Publication Data

US 2006/0149073 A1    Jul. 6, 2006

(30) Foreign Application Priority Data

Dec. 25, 2002   (JP) ............................. 2002-374659

(51) Int. Cl.
*C07C 43/18* (2006.01)
(52) U.S. Cl. .................................... 568/665
(58) Field of Classification Search .................. 568/665
See application file for complete search history.

(56) References Cited

U.S. PATENT DOCUMENTS 6,440,636 B1   8/2002   Ushirogouchi et al.
2002/0115883 A1   8/2002   Ogata et al.

FOREIGN PATENT DOCUMENTS

DE   119 008   3/1901
WO   02/36533   5/2002

OTHER PUBLICATIONS

McMurry, John "Organic Chemistry—Fourth Edition" Brooks/Cole Publishing Company, 1996, pp. 816-818.*
Okada et al. "Amino Acids and Peptides. L. Development of a Novel N-pi-Protecting Group for Histidine, N-pi-2-Adamantyloxymethylhistidine, and Its Application to Peptide Synthesis" Chem Pharm Bull, 1997, vol. 45, pp. 452-456.*
Ben-David et al. "A novel synthesis of trifluoromethyl ethers via xanthates, utilizing BrF3" Journal of Fluorine Chemistry, 1999, vol. 97, pp. 75-78.*
Machula, A. A. et al., "Radiochemical alkylation of adamantane by perfluorovinyl ethers", Khimiya Vysokikh Energii, vol. 24, No. 2, pp. 117-121, 1990.
Database Crossfire Beilstein, Beilstein Institut zur Foerderung der Chemischen Wissenschaften, XP002367361, Palfray, Sabetay: Bull. Soc. Chim. Fr., <4> 43, p. 900, 1928.
Farren, J.W. et al., Chloro Ethers. II. Preparation of Some New Chloro Ethers and Alkoxymethyl Esters, J. AM. Chem. Soc., vol. 47, pp. 2419-2423, 1925.
Ben-David, Iris et al., "A novel synthesis of trifluoromethyl ethers via xanthates, utilizing BrF3", Journal of Fluorine Chemistry, vol. 97, No. 1-2, pp. 75-78, 1999. 0009.
Okada, Yoshio et al., "Amino acids and peptides. L. Development of a Novel Nπ-protecting group for histidine, Nπ-adamantyloxymethylhistidine, and its application to peptide synthesis", Chemical and Pharmaceutical Bulletin, vol. 45, No. 3, pp. 452 to 456, 1997.
Moss, Robert A. et al., "Absolute Kinetics of Alkoxychlorocarbene Fragmentation", Journal of the American Chemical Society, vol. 118, No. 40, pp. 9792 to 9793, 1996.
Rykov, S.V. et al., Photochemical reactions of some mono- and diketo derivatives of adamantane in different solvents, Izvestiya Akademii Nauk, Seriya Kimicheskaya, No. 9, pp. 1833 to 1835. 0039.
Pericas, Miquel A. et al., Efficient synthesis of tert-alkoxy ethynes, Tetrahedron, vol. 43, No. 10, 2311 to 2316.

* cited by examiner

*Primary Examiner*—Rei-tsang Shiao
*Assistant Examiner*—Joseph R Kosack
(74) *Attorney, Agent, or Firm*—Oblon, Spivak, McClelland, Maier & Neustadt, P.C.

(57) ABSTRACT

Provided is an adamantane derivative represented by Formula (I) or (II):

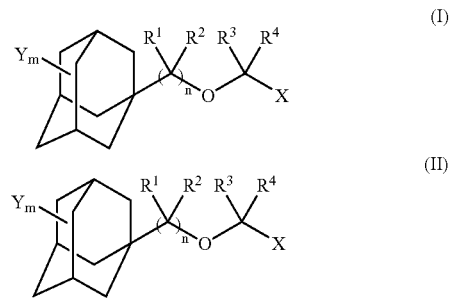

wherein X represents a halogen atom; Y represents an alkyl group having 1 to 10 carbon atoms, a halogenated alkyl group having 1 to 10 carbon atoms, a halogen atom or a hetero atom-containing group; $R^1$ to $R^4$ represent independently hydrogen, a halogen atom, an alkyl group having 1 to 10 carbon atoms or a halogenated alkyl group having 1 to 10 carbon atoms; m represents an integer of 0 to 15, and n represents an integer of 0 to 10; and excluded is a case where in Formula (I), m and n are 0 at the same time and $R^3$ and $R^4$ are a hydrogen atom at the same time.

Capable of being provided is a novel adamantane derivative which is useful as a modifying agent for a resin for a photoresist and a dry etching resistance-improving agent in the photolithography field, agricultural and medical intermediates and other various industrial products.

3 Claims, No Drawings

ADAMANTANE DERIVATIVE AND PROCESS FOR PRODUCING THE SAME

BACKGROUND OF THE INVENTION

The present invention relates to a novel adamantane derivative and a process for producing the same. More specifically, the present invention relates to novel (monohalogen-substituted methyl) (adamantyl group-containing alkyl)ethers which are useful as a modifying agent for a resin for a photoresist and a dry etching resistance-improving agent in the photolithography field, agricultural and medical intermediates and other various industrial products and a process for efficiently producing the same.

RELATED ART

It is known that adamantane is a highly symmetric and stable compound having a structure in which four cyclohexane rings are condensed in a cage form and that the derivatives thereof are useful as agricultural and medical raw materials and a raw material for high functional-industrial materials since it shows a specific function. For example, it has an optical characteristic and a heat resistance, so that it is tried to be used for an optical disc substrate, an optical fiber and a lens (refer to, for example, Japanese Patent Application Laid-Open No. 305044/1994 and Japanese Patent Application Laid-Open No. 302077/1997).

Further, adamantane esters are tried to be used as a resin raw material for a photoresist making use of an acid sensitivity, a dry etching resistance and a UV ray transmittance thereof (refer to, for example, Japanese Patent Application Laid-Open No. 39665/1992).

On the other hand, as a semiconductor element is progressively fined in recent years, it is required to be further fined at a lithography step in the production thereof, and therefore investigated are various methods for forming fine patterns using photoresist materials corresponding to irradiated beams having a short wavelength such as KrF, ArF and $F_2$ eximer laser beams. A novel photoresist material which can correspond to irradiated beams having a short wavelength such as the eximer laser beam and the like described above has been desired to be developed.

DISCLOSURE OF THE INVENTION

The present invention has been made under the situations described above, and an object of the present invention is to provide a novel adamantane derivative which is useful as a modifying agent for a resin for a photoresist and a dry etching resistance-improving agent in the photolithography field, agricultural and medical intermediates and other various industrial products and a process for producing the same.

Intensive researches repeated by the present inventors in order to achieve the object described above have resulted in finding that (monohalogen-substituted methyl) (adamantyl group-containing alkyl)ethers having a specific structure are novel compounds which are not described in documents and can meet the above object and that these compounds can efficiently be produced by reacting corresponding alcohols used as the raw materials. The present invention has been completed based on such knowledge.

That is, the present invention comprises the following scope.
1. An adamantane derivative characterized by having a structure represented by Formula (I) or (II):

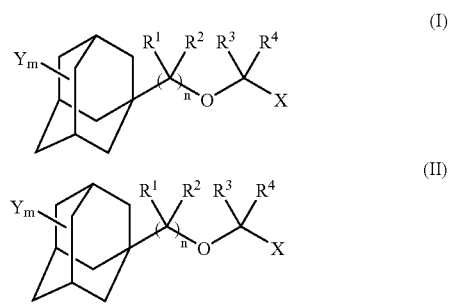

wherein X represents a halogen atom; Y represents an alkyl group having 1 to 10 carbon atoms, a halogenated alkyl group having 1 to 10 carbon atoms, a halogen atom or a hetero atom-containing group; $R^1$ to $R^4$ represent independently hydrogen, a halogen atom, an alkyl group having 1 to 10 carbon atoms or a halogenated alkyl group having 1 to 10 carbon atoms; m represents an integer of 0 to 15, and n represents an integer of 0 to 10; and excluded is a case where in Formula (I), m and n are 0 at the same time and $R^3$ and $R^4$ are a hydrogen atom at the same time.

2. The adamantane derivative as described in the above item 1, wherein in Formula (I) or (II) described above, Y represents =O formed by allowing two Y's to be put together.

3. A production process for the adamantane derivative as described in the above item 1 or 2, characterized by reacting alcohol having an adamantyl group represented by Formula (III) or (IV):

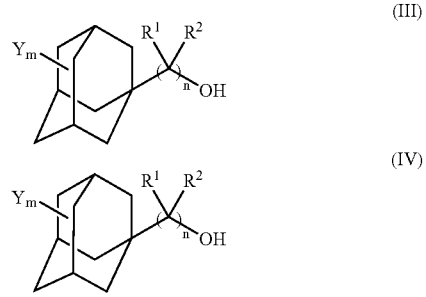

(wherein X, Y, $R^1$, $R^2$, m and n are the same as described above) with a carbonyl compound represented by Formula (V):

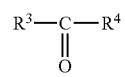

(wherein $R^3$ and $R^4$ are the same as described above, and when m and n are 0 at the same time in Formula (III) described above, $R^3$ and $R^4$ are not a hydrogen atom at the same time) and hydrogen halide gas.

4. A production process for the adamantane derivative as described in the above item 1 or 2, characterized by reacting alcohol having an adamantyl group represented by Formula (III) or (IV):

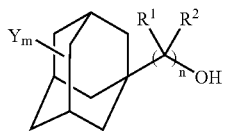
(III)

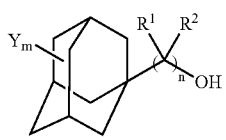
(IV)

(wherein X, Y, R¹, R², m and n are the same as described above, and a case where m and n are 0 at the same time in Formula (III) is excluded) with dimethylsulfoxide under the presence of acetic anhydride to obtain a (methylthio)methyl ether compound and reacting it with sulfuryl chloride after isolating it or without isolating it.

BEST MODE FOR CARRYING OUT THE INVENTION

The adamantane derivatives of the present invention are the compound represented by Formula (I) (hereinafter referred to as the compound A) and the compound represented by Formula (II) (hereinafter referred to as the compound B), and both of them are novel compounds which are not described in documents. The compound A, the compound B and the production processes for the same shall be explained below.

First, the compound A of the present invention is (monohalogen-substituted methyl) (adamantyl group-containing alkyl)ethers having a structure represented by Formula (I):

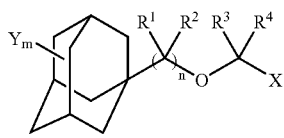
(I)

In Formula (I) described above, X represents a halogen atom; Y represents an alkyl group having 1 to 10 carbon atoms, a halogenated alkyl group having 1 to 10 carbon atoms, a halogen atom or a hetero atom-containing group; R¹ to R⁴ represent independently hydrogen, a halogen atom, an alkyl group having 1 to 10 carbon atoms or a halogenated alkyl group having 1 to 10 carbon atoms; m represents an integer of 0 to 15, and n represents an integer of 0 to 10. Excluded is a case where m and n are 0 at the same time and R³ and R⁴ are a hydrogen atom at the same time.

In the matter described above, the halogen atom includes fluorine, chlorine, bromine and iodine. The alkyl group having 1 to 10 carbon atoms may be either linear or branched. The halogenated alkyl group having 1 to 10 carbon atoms may be a group in which the foregoing alkyl group having 1 to 10 carbon atoms is substituted with at least one halogen group in a suitable position thereof. The hetero atom-containing group is a substituent containing O (oxygen), S (sulfur) or N (nitrogen). For example, it can be represented by the following formula:

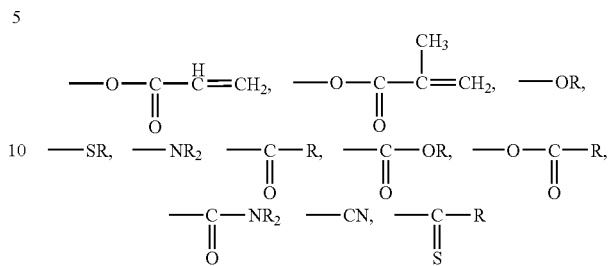

(wherein R represents independently hydrogen, a halogen atom, an alkyl group having 1 to 10 carbon atoms or a halogenated alkyl group having 1 to 10 carbon atoms).

The hetero atom-containing group may be =O formed by allowing two Y's to be put together.

The compound A represented by Formula (I) described above includes, for example, the following compounds:

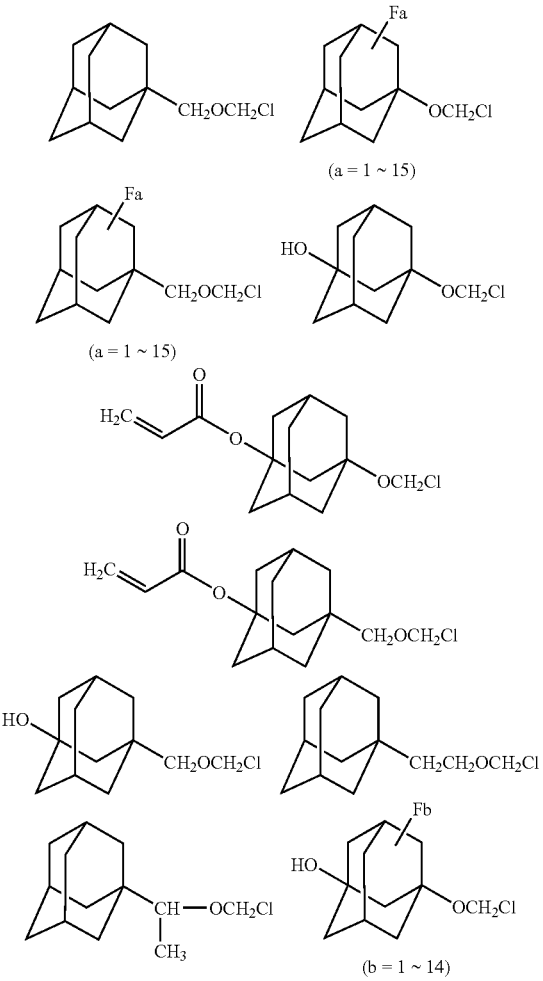

When Y represents =O formed by allowing two Y's to be put together in Formula (I) described above, capable of being given are (chloromethyl) (2-oxo-1-adamantyl)ether, (chloromethyl) (4-oxo-1-adamantyl)ether, (chloromethyl) (3,5- dimethyl-2-oxo-1-adamantyl)ether, (chloromethyl) (3,5-dimethyl-4-oxo-1-adamantyl)ether, (chloromethyl) (3,7-dimethyl-2-oxo-1-adamantyl)ether, (chloromethyl) (3,7-dimethyl-4-oxo-1-adamantyl)ether, (chloromethyl) (2-oxo-1-adamantylmethyl)ether, (chloromethyl) (4-oxo-1-adamantylmethyl)ether, (chloromethyl) (2-oxo-1-perfluoroadamantyl)ether, (chloromethyl) (4-oxo-1-perfluoroadamantyl)ether, (chloromethyl) (2-oxo-1-perfluoroadamantylmethyl)ether and (chloromethyl) (4-oxo-1-perfluoroadamantylmethyl)ether.

Next, the compound B of the present invention is (monohalogen-substituted methyl) (adamantyl group-containing alkyl)ethers having a structure represented by Formula (II):

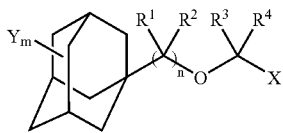
(II)

In Formula (II) described above, X, Y, $R^1$ to $R^4$, m and n are the same as described above. In this case, included is a case where m and n are 0 at the same time and $R^3$ and $R^4$ are a hydrogen atom at the same time.

The compound B represented by Formula (II) described above includes, for example, the following compounds:

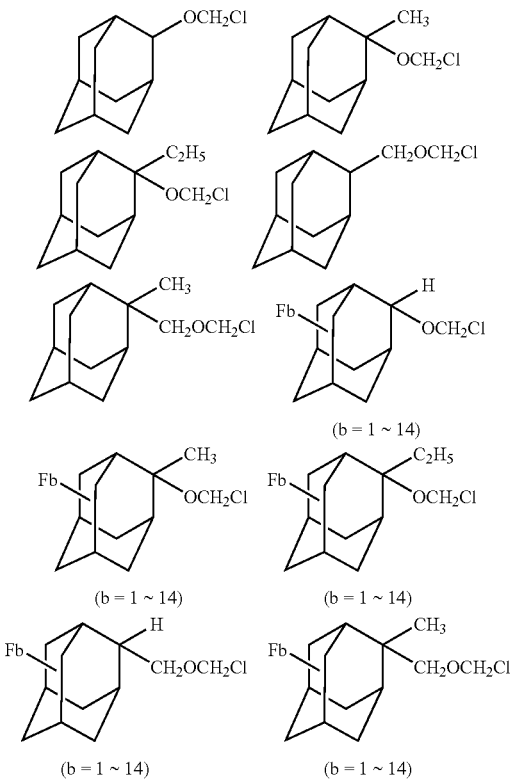

When Y represents =O formed by allowing two Y's to be put together in Formula (II) described above, capable of being given are (chloromethyl) (4-oxo-2-adamantyl)ether, (chloromethyl) (3,5-dimethyl-4-oxo-2-adamantyl)ether, (chloromethyl) (3,7-dimethyl-2-oxo-1-adamantyl)ether, (chloromethyl) (3,7-dimethyl-4-oxo-2-adamantyl)ether, (chloromethyl) (2-methyl-4-oxo-2-adamantyl) ether, (chloromethyl) (2-ethyl-4-oxo-2-adamantyl)ether, (chloromethyl) (4-oxo-2-adamantylmethyl)ether, (chloromethyl) (4-oxo-2-perfluoroadamantyl)ether and (chloromethyl) (4-oxo-2-perfluoroadamantylmethyl)ether.

Next, the production processes of the compounds A and B of the present invention described above shall be explained. The production processes include the following two processes.

That is, they are a process in which alcohol (hereinafter referred to as the raw material alcohol) having an adamantyl group represented by Formula (III) or (IV) described above is reacted with a carbonyl compound represented by Formula (V):

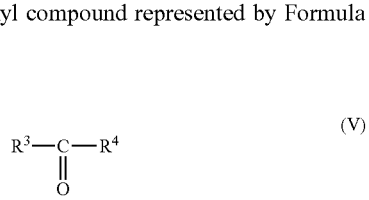
(V)

(wherein $R^3$ and $R^4$ are the same as described above, and when m and n are 0 at the same time in Formula (III) described above, $R^3$ and $R^4$ are not a hydrogen atom at the same time) and hydrogen halide gas (production process 1) and a process in which the raw material alcohol is reacted with dimethylsulfoxide under the presence of acetic anhydride to obtain a (methylthio)methyl ether compound and in which it is reacted with sulfuryl chloride after isolating it or without isolating it (production process 2). In the production process 2, a case where m and n are 0 at the same time in Formula (III) described above is excluded.

In respect to the raw material alcohol used in the two production processes described above, first, the raw material alcohol for the compound A includes the following compounds represented by Formula (III) described above:

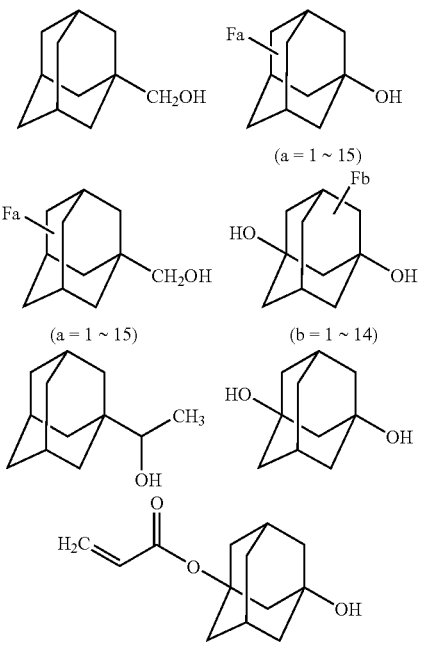

-continued

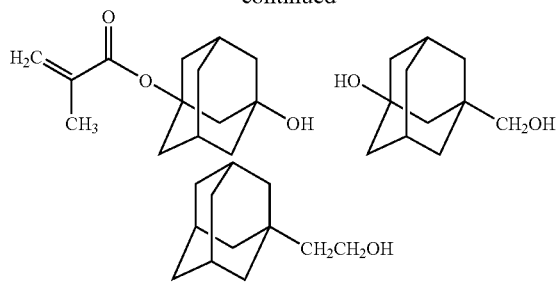

When Y represents =O formed by allowing two Y's to be put together in Formula (III) described above, capable of being given are 2-oxo-1-adamantanol, 4-oxo-1-adamantanol, 3,5-dimethyl-2-oxo-1-adamantanol, 3,5-dimethyl-4-oxo-1-adamantanol, 3,7-dimethyl-2-oxo-1-adamantanol, 3,7-dimethyl-4-oxo-1-adamantanol, 2-oxo-1-adamantylmethanol, 4-oxo-1-adamantylmethanol, 2-oxo-1-perfuloroadamantanol, 4-oxo-1-perfuloroadamantanol, 2-oxo-1-perfuloroadamantylmethanol and 4-oxo-1-perfuloroadamantylmethanol.

Next, the raw material alcohol for the compound B includes the following compounds represented by Formula (IV) described above:

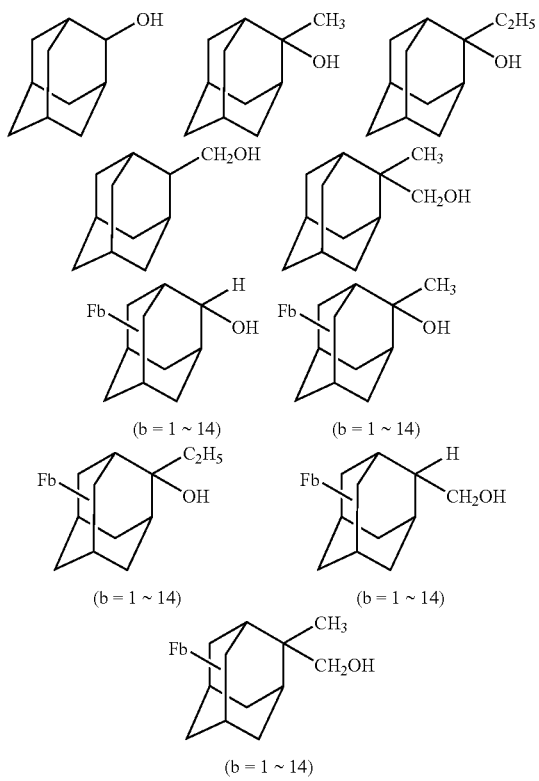

When Y represents =O formed by allowing two Y's to be put together in Formula (IV) described above, capable of being given are 4-oxo-2-adamantanol, 3,5-dimethyl-4-oxo-2-adamantanol, 3,5-dimethyl-4-oxo-2-adamantanol, 3,7-dimethyl-4-oxo-2-adamantanol, 2-methyl-4-oxo-2-adamantanol, 2-ethyl-4-oxo-2-adamantanol, 4-oxo-2-adamantylmethanol, 4-oxo-2-perfuloroadamantanol and 4-oxo-2-perfuloroadamantanemethanol.

Subsequently, the two production processes shall be explained in details.

(1) Production Process 1

After the raw material alcohol and the carbonyl compound are molten or diluted by a solvent, a desiccant is added thereto, and dried hydrogen halide gas is blown thereinto to react them.

The carbonyl compound described above includes formaldehyde (paraformaldehyde), acetaldehyde, acetone, propionaldehyde, n-butylaldehyde, isobutylaldehyde, ethyl methyl ketone, isopropyl methyl ketone, isobutyl methyl ketone and diethyl ketone. An amount of the carbonyl compound is usually 1 to 5 moles per mole of the raw material alcohol.

Conventional desiccants can be used as the desiccant described above. To be specific, it includes anhydrous inorganic salts such as anhydrous magnesium sulfate, anhydrous iron chloride and anhydrous aluminum chloride, calcium chloride, molecular sieves, diphosphorus pentaoxide, sodium perchlorate, activated alumina, silica gel, calcium hydride and lithium aluminum hydride. An amount of the desiccant is usually 0.5 to 5 moles per mole of the raw material alcohol.

Hydrogen halide gas is preferably dried. Capable of being adopted are a method in which it is supplied from a commercial bomb and a method in which hydrogen halide gas produced by reacting sodium halide with conc. sulfuric acid is supplied. An amount of the hydrogen halide gas is usually 1 to 20 moles per mole of the raw material alcohol. In general, hydrogen chloride gas is used as the hydrogen halide gas.

A solvent may not be used, but when it is used, a solvent having a solubility of 0.5 mass % or more, preferably 5 mass % or more for the raw material alcohol may be used. To be specific, it includes hydrocarbon base solvents such as hexane and heptane; ether base solvents such as diethyl ether and THF; and halogen base solvents such as dichloromethane and carbon tetrachloride. An amount of the solvent is such an amount that a concentration of the raw material alcohol in the reaction mixture is usually 0.5 mass % or more, preferably 5 mass % or more. In this case, the raw material alcohol may stay in a suspension state but is preferably dissolved. Moisture contained in the solvent is preferably removed before use.

In respect to the reaction conditions, the reaction temperature is usually −200 to 200° C., preferably −78 to 50° C. If the temperature is too low, the reaction rate is reduced, and the reaction time is extended. If the temperature is too high, side reactions are increased, and hydrogen chloride gas is reduced in a solubility in the solvent, which results in requiring a large amount of hydrogen chloride gas. Accordingly, both are not preferred. The reaction pressure is usually 0.01 to 10 MPa, preferably atmospheric pressure to 1 MPa in terms of absolute pressure. If the pressure is too low, hydrogen chloride gas is reduced in a solubility, and the reaction time is extended. If the pressure is too high, a specific pressure proofing apparatus is required, and it is not economical. The reaction time is usually 1 minute to 24 hours, preferably 30 minutes to 5 hours.

Distillation, crystallization and separation by a column can be adopted for refining the intended reaction product, and the refining method can be selected according to the properties of the product and the kind of impurities.

(2) Production Process 2

The raw material alcohol and dimethylsulfoxide are mixed and heated under the coexistence of acetic anhydride to produce a (methylthio)methyl ether compound (hereinabove, a front stage step), and the (methylthio)methyl ether compound thus obtained is reacted with sulfuryl chloride to obtain the intended chlorinated methyl ether compound (hereinabove, a rear stage step).

Front Stage Step

An amount of dimethylsulfoxide is usually 1 to 1,000 moles per mole of the raw material alcohol.

An amount of acetic anhydride is usually 1 to 1,000 moles, preferably 2 to 100 moles per mole of the raw material alcohol. A solvent may not be used, but when it is used, it includes, to be specific, hydrocarbon base solvents such as hexane and heptane; ether base solvents such as diethyl ether and THF; and halogen base solvents such as dichloromethane and carbon tetrachloride. An amount of the solvent may be such an amount that a concentration of the raw material alcohol is 1 to 50 mass %.

In respect to the reaction conditions, the reaction temperature is usually −200 to 200° C., preferably −78 to 50° C. If the temperature is too low, the reaction rate is reduced, and the reaction time is extended. If the temperature is too high, side reactions are increased. Accordingly, both are not preferred. The reaction pressure is usually 0.01 to 10 MPa, preferably atmospheric pressure in terms of absolute pressure. The reaction time is usually 6 hours to 14 days, preferably 1 to 7 days.

In respect to the after-treatment, first the reaction mixture is poured into a saturated sodium hydrogencarbonate aqueous solution. Solid sodium hydrogencarbonate is added thereto while stirring until foaming is not observed. Further, sodium hydroxide and diethyl ether are added thereto and stirred for 3 hours to 3 days. The diethyl ether layer is separated, and then the aqueous layer is further extracted with diethyl ether. Subsequently, the diethyl ether solution is mixed therewith, and after drying, diethyl ether is distilled off to obtain a crude product.

Distillation, crystallization and separation by a column can be adopted for refining the reaction product, and the refining method can be selected according to the properties of the product and the kind of impurities. Or, it can be used for reaction in the rear stage step without refining.

Rear Stage Step

A solvent may not be used, but when it is used, it includes, to be specific, hydrocarbon base solvents such as hexane and heptane; ether base solvents such as diethyl ether and THF; and halogen base solvents such as dichloromethane and carbon tetrachloride. An amount of the solvent may be such an amount that a concentration of the (methylthio)methyl ether compound is 1 to 50 mass %.

In respect to the reaction method, there can be adopted a method in which sulfuryl chloride is dropwise added while stirring the crude liquid or the (methylthio)methyl ether compound dissolved in a solvent.

In respect to the reaction conditions, the reaction temperature is usually −200 to 100° C., preferably −78 to 30° C. If the temperature is too low, the reaction rate is reduced, and the reaction time is extended. If the temperature is too high, side reactions are increased. Accordingly, both are not preferred. The reaction pressure is usually 0.01 to 10 MPa, preferably atmospheric pressure in terms of absolute pressure. The reaction time is usually 1 minute to 24 hours, preferably 30 minutes to 5 hours.

In respect to the after-treatment, the solvent and the light by-products can be removed by evaporation.

Distillation, crystallization and separation by a column can be adopted for refining the intended reaction product, and the refining method can be selected according to the properties of the product and the kind of impurities.

The adamantane derivative [(monohalogen-substituted methyl) (adamantyl group-containing alkyl)ethers] of the present invention can efficiently be produced in the manner described above.

The compound thus obtained can be identified by means of gas chromatography (GC), liquid chromatography (LC), gas chromatography mass spectrometry (GC-MS), nuclear magnetic resonance spectrometry (NMR), infrared spectrometry (IR) and a melting point measuring apparatus.

EXAMPLES

Next, the present invention shall be explained in further details with reference to examples, but the present invention shall by no means be restricted by these examples.

Example 1

Synthesis of (chloromethyl) (1-adamantylmethyl)ether represented by a structural formula

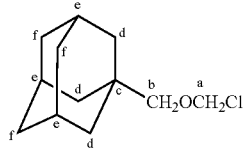

A Kjeldahl flask having a volume of 50 ml equipped with a nozzle for introducing hydrogen chloride gas was charged with 1.66 g (10 mmol) of 1-adamantylmethanol, 0.60 g (20 mmol) of paraformaldehyde, 1.20 g (10 mmol) of magnesium sulfate and 30 ml of dried dichloromethane, and it was cooled to 0° C. on an ice bath and stirred. Hydrogen chloride gas generated by mixing 10 g of sodium chloride with 50 ml of conc. sulfuric acid was blown thereinto through the nozzle for one hour. After further stirring for 60 minutes, magnesium sulfate was filtered, and then the solution was analyzed by gas chromatography to confirm that 1-adamantylmethanol was completely converted and that the intended product was obtained at a selectivity of 94.5%. Hydrogen chloride and dichloromethane were removed, and then refining was carried out by distillation to isolate 1.87 g (8.72 mmol, yield 87.2%) of the intended product.

The analytical results of the above compound are shown below.

Nuclear magnetic resonance spectrometry (NMR): $CDCl_3$
$^1$H-NMR (500 MHz): 1.53 (6H, f), 1.64 to 1.72 (6H, d), 1.97 (3H, e), 3.25 (2H, b), 5.50 (2H, a), $^{13}$C-NMR (126 MHz): 28.18 (e), 37.11 (d or f), 39.45 (d or f), 33.49 (c), 81.34 (b), 84.25 (a)

Infrared spectrometry (IR): 2905 cm$^{-1}$ (C—H; str.), 1157 cm$^{-1}$ (C—O—C; str.), 650 cm$^{-1}$ (C—Cl; str.)

Boiling point (bp): 130 to 133° C./0.7 kPa

Example 2

Synthesis of (chloromethyl) (4-oxo-2-adamantyl)Ether Represented by a Structural Formula

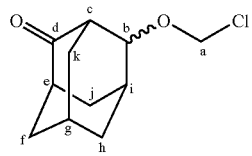

A separable flask having a volume of one liter equipped with a nozzle for introducing hydrogen chloride gas was equipped with a stirring device and charged with 50.0 g (301 mmol) of 4-oxo-2-adamantanol, 13.6 g (450 mmol) of paraformaldehyde, 36.2 g (300 mmol) of magnesium sulfate and 650 ml of dried dichloromethane, and it was cooled to 0° C. on an ice bath and stirred. Hydrogen chloride gas generated by mixing 300.7 g (5 mole) of sodium chloride with 700 ml of conc. sulfuric acid was blown thereinto through the nozzle for one hour. After further stirring for 3 hours, magnesium sulfate was filtered, and then the solution was analyzed by gas chromatography to confirm that 4-oxo-2-adamantanol was completely converted and that the intended product was obtained at a selectivity of 93.2%. Hydrogen chloride and dichloromethane were removed, and then refining was carried out by distillation to isolate 55.0 g (256 mmol, yield 85.2%, GC purity 98.8%) of the intended product.

The analytical results of the above compound are shown below.

Nuclear magnetic resonance spectrometry (NMR): $CDCl_3$ $^1$H-NMR (500 MHz): 1.66 to 1.69 (m), 1.75 to 1.78 (m), 1.89 to 2.12 (m), 2.20 (m), 2.25 (m), 2.82 (m), 2.40 (dq, J=13.0 Hz, 2.8 Hz), 2.51 (s), 2.54 (s), 2.79 (s), 3.94 (t, J=3.5 Hz, 1H, $b^2$), 4.31 (q, J=2.7 Hz, 1H, $b^1$), 5.52 (s, 2H, $a^1$), 5.55 (dd, J=5.4 Hz, 17.6 Hz, 2H, $a^2$), $^{13}$C-NMR (127 MHz): 26.26 ($g^1$), 26.39 ($g^2$) 29.98 ($f^2$ or $h^2$ or $j^2$ or $k^2$), 30.95 ($i^2$), 31.26 ($i^1$), 32.46 ($f^2$ or $h^2$ or $j^2$ or $k^2$), 32.98 ($f^1$ or $h^1$ or $j^1$ or $k^1$), 33.44 ($f^2$ or $h^2$ or $j^2$ or $k^2$), 34.99 ($f^1$ or $h^1$ or $j^1$ or $k^1$), 37.80 ($f^1$ or $h^1$ or $j^1$ or $k^1$), 38.68 ($f^2$ or $h^2$ or $j^2$ or $k^2$), 38.78 ($f^1$ or $h^1$ or $j^1$ or $k^1$), 45.31 ($e^2$), 46.18 ($e^1$), 50.52 ($c^1$), 51.07 ($c^2$), 79.69 ($b^1$), 79.82 ($a^2$), 80.44 ($b^2$), 83.97 ($a^1$), 213.86 ($d^2$) 214.96 ($d^1$) (superscript numeral 1 represents a principal isomer, and superscript numeral 2 represents a subsidiary isomer)

Gas chromatography mass spectrometry (GC-MS): EI 216 ($M^+$+2, 2.9%), 214 ($M^+$, 8.7%), 148 (29.2%), 79 (100%)

Boiling point: 160 to 161° C./0.2 kPa

INDUSTRIAL APPLICABILITY

The adamantane derivatives of the present invention are novel (monohalogen-substituted methyl) (adamantyl group-containing alkyl)ethers, and they are useful as a modifying agent for a resin for a photoresist and a dry etching resistance-improving agent in the photolithography field, agricultural and medical intermediates and other various industrial products.

What is claimed is:

1. A substituted adamantane of Formula (I) or (II):

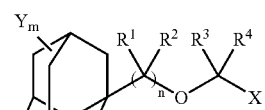

(I)

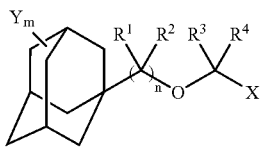

(II)

wherein

X represents a halogen atom;

Y is a $C_1$-$C_{10}$ alkyl group, a halogenated $C_1$-$C_{10}$ alkyl group, a halogen atom or a hetero atom-containing group;

$R^1$ and $R^2$ represents, independently, hydrogen, a halogen atom, a $C_1$-$C_{10}$ alkyl group or a halogenated $C_1$-$C_{10}$ alkyl group;

$R^3$ and $R^4$ represent, independently, hydrogen, a $C_1$-$C_{10}$ alkyl group, or a $C_1$-$C_{10}$ halogenated alkyl group, wherein $R^3$ and $R^4$ cannot both be hydrogen in Formula (I);

wherein, in the formula (I), m represents an integer of 0 to 15, and n represents an integer of 1 to 10;

wherein, in the Formula (II), m represents an integer of 1 to 15.

2. A substituted adamantane selected from the group consisting of

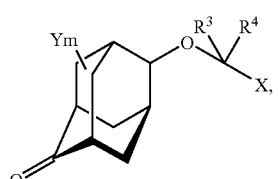

(IIa)

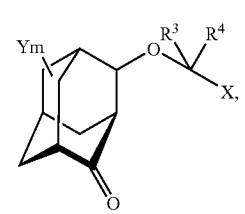

(IIb)

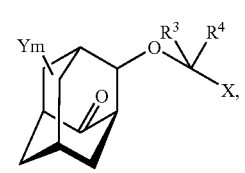

(IIc)

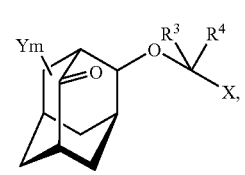

(IId)

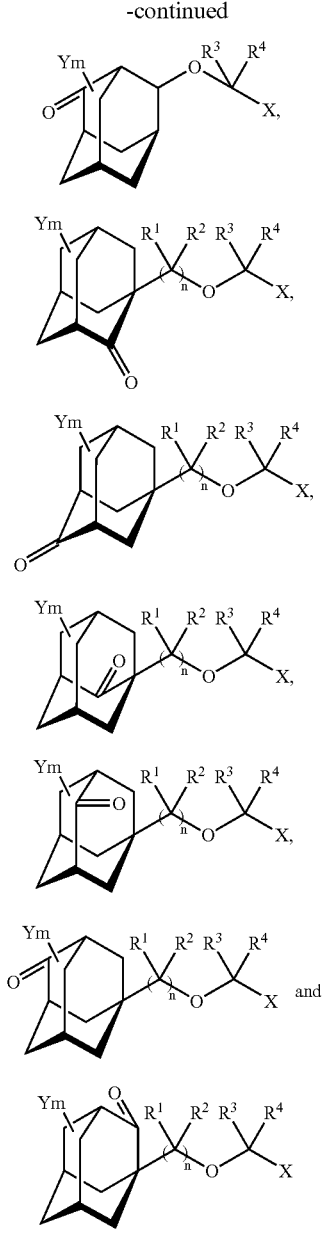

wherein
X represents a halogen atom;
Y is a $C_1$-$C_{10}$ alkyl group, a halogenated $C_1$-$C_{10}$ alkyl group, a halogen atom or a hetero atom-containing group;
$R^1$ and $R^2$ represent, independently, hydrogen, a halogen atom, a $C_1$-$C_{10}$ alkyl group or a halogenated $C_1$-$C_{10}$ alkyl group;
$R^3$ and $R^4$ represent, independently, hydrogen, a $C_1$-$C_{10}$ alkyl group, or a $C_1$-$C_{10}$ halogenated alkyl group,
wherein $R^3$ and $R^4$ cannot both be hydrogen in Formulae (Ia-If);
wherein, in the formulae (Ia-If), m represents an integer of 0 to 13, and n represents an integer of 1 to 10;
wherein, in the Formula (IIa-IIe), m represents an integer of 1 to 13.

3. A process for producing the substituted adamantane of claim 1, comprising
reacting an alcohol comprising an adamantyl group represented by Formula (III) or (IV):

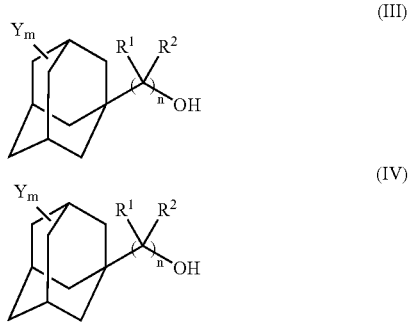

wherein in Formula (III), n represents an integer of 1 to 10; with a carbonyl compound represented by Formula (V):

and at least one hydrogen halide gas; wherein $R^3$ and $R^4$ in Formula (V) are not both hydrogen when the carbonyl compound of formula (V) is reacted with the adamantyl group of Formula (III), and wherein m represents an integer of 1 to 13.

* * * * *

UNITED STATES PATENT AND TRADEMARK OFFICE
CERTIFICATE OF CORRECTION

PATENT NO. : 7,470,824 B2  
APPLICATION NO. : 10/540547  
DATED : December 30, 2008  
INVENTOR(S) : Tanaka et al.

It is certified that error appears in the above-identified patent and that said Letters Patent is hereby corrected as shown below:

On the title page, Item (87) should read:

--(87) PCT Pub. No.: WO2004/058675  
       PCT Pub. Date: Jul. 15, 2004--

Signed and Sealed this

Seventeenth Day of February, 2009

JOHN DOLL  
*Acting Director of the United States Patent and Trademark Office*

UNITED STATES PATENT AND TRADEMARK OFFICE
CERTIFICATE OF CORRECTION

PATENT NO. : 7,470,824 B2 Page 1 of 1
APPLICATION NO. : 10/540547
DATED : December 30, 2008
INVENTOR(S) : Shinji Tanaka et al.

It is certified that error appears in the above-identified patent and that said Letters Patent is hereby corrected as shown below:

Column 12, Claim 1, lines 11-16, should read:

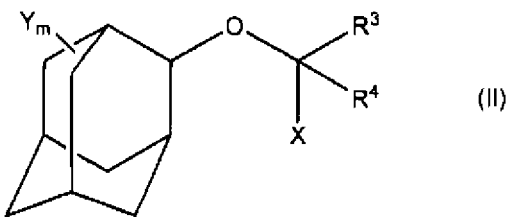

Column 14, Claim 3, lines 28-33, should read:

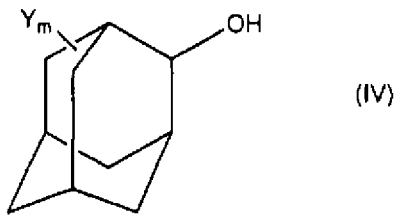

Signed and Sealed this

Thirteenth Day of October, 2009

David J. Kappos
*Director of the United States Patent and Trademark Office*